(12) United States Patent
Lundsgaard et al.

(10) Patent No.: US 6,605,471 B1
(45) Date of Patent: Aug. 12, 2003

(54) METHOD AND SYSTEM FOR DETERMINING AT LEAST ONE PARAMETER OF AT LEAST ONE SAMPLE OF A PHYSIOLOGICAL LIQUID, A HOLDER AND A TEST DEVICE

(75) Inventors: Finn C. Lundsgaard, Taastrup (DK); Henrik Kagenow, Holstebro (DK); Willy Andersen, Espergaerde (DK); Peter Aage Frischauf, Brondby (DK)

(73) Assignee: Radiometer Medical A/S, Brønshøj (DK)

( * ) Notice: Subject to any disclaimer, the term of this patent is extended or adjusted under 35 U.S.C. 154(b) by 0 days.

(21) Appl. No.: 09/194,372

(22) PCT Filed: May 27, 1997

(86) PCT No.: PCT/DK97/00238

§ 371 (c)(1),
(2), (4) Date: Apr. 21, 1999

(87) PCT Pub. No.: WO97/46887

PCT Pub. Date: Dec. 11, 1997

(30) Foreign Application Priority Data

May 30, 1996 (DK) .............................................. 0615/96

(51) Int. Cl.[7] ........................ G01N 21/11; G01N 21/13
(52) U.S. Cl. ........................ 436/165; 436/45; 436/47; 436/48; 436/63; 436/163; 436/164; 436/174; 422/55; 422/58; 422/61; 422/64; 422/81; 422/82.05; 422/82.08; 422/102; 422/104
(58) Field of Search .......................... 422/55, 58, 61, 422/64, 81, 82.05, 82.08, 102, 104; 436/47, 45, 48, 63, 163, 164, 174, 165

(56) References Cited

U.S. PATENT DOCUMENTS

| | | | |
|---|---|---|---|
| 4,007,013 A | 2/1977 | Kotacka | |
| 4,053,381 A | 10/1977 | Hambien et al. | |
| 4,218,421 A | 8/1980 | Mack, Jr. et al. | |
| 4,269,803 A | 5/1981 | Jessop | |
| 4,301,412 A | 11/1981 | Hill et al. | |
| 4,318,994 A | * 3/1982 | Meyer et al. | 435/301 |
| 4,424,191 A | * 1/1984 | Jakubowicz | 422/65 |
| 4,497,774 A | * 2/1985 | Scordato | 422/73 |
| 5,340,747 A | * 8/1994 | Eden | 436/172 |
| 5,371,020 A | 12/1994 | Frischauf | |
| 5,374,395 A | * 12/1994 | Robinson et al. | 422/64 |
| 5,436,129 A | * 7/1995 | Stapleton | 435/6 |
| 5,489,414 A | 2/1996 | Schreiber et al. | |
| 5,504,011 A | * 4/1996 | Gavin et al. | 436/69 |
| 5,510,266 A | * 4/1996 | Bonner et al. | 436/43 |
| 5,601,991 A | * 2/1997 | Oberhardt | 435/7.91 |
| 5,670,375 A | * 9/1997 | Seaton et al. | 436/48 |
| 5,688,695 A | * 11/1997 | Kramer | 436/164 |

FOREIGN PATENT DOCUMENTS

| | | |
|---|---|---|
| EP | 534 945 | 6/1990 |
| EP | 390 315 | 10/1990 |
| EP | 502 691 | 9/1992 |
| EP | 449 899 | 9/1994 |
| GB | 2090659 | 7/1982 |
| WO | WO 89/04474 | 5/1989 |
| WO | WO 89/04955 | 6/1989 |
| WO | WO 90/02938 | 3/1990 |
| WO | WO 90/07106 | 6/1990 |

* cited by examiner

*Primary Examiner*—Jill Warden
*Assistant Examiner*—Kathryn Bex
(74) *Attorney, Agent, or Firm*—Bryan Cave LLP; Maurice B. Stiefel

(57) ABSTRACT

The present invention relates to a method for determining at least one parameter of samples of physiological liquids, to test devices which may be used in the method, to a holder comprising a plurality of such test devices, and to a measuring apparatus adapted to accommodate the holder and to be used in the method and to a system comprising the apparatus and the holder.

6 Claims, 6 Drawing Sheets

Figure 1:
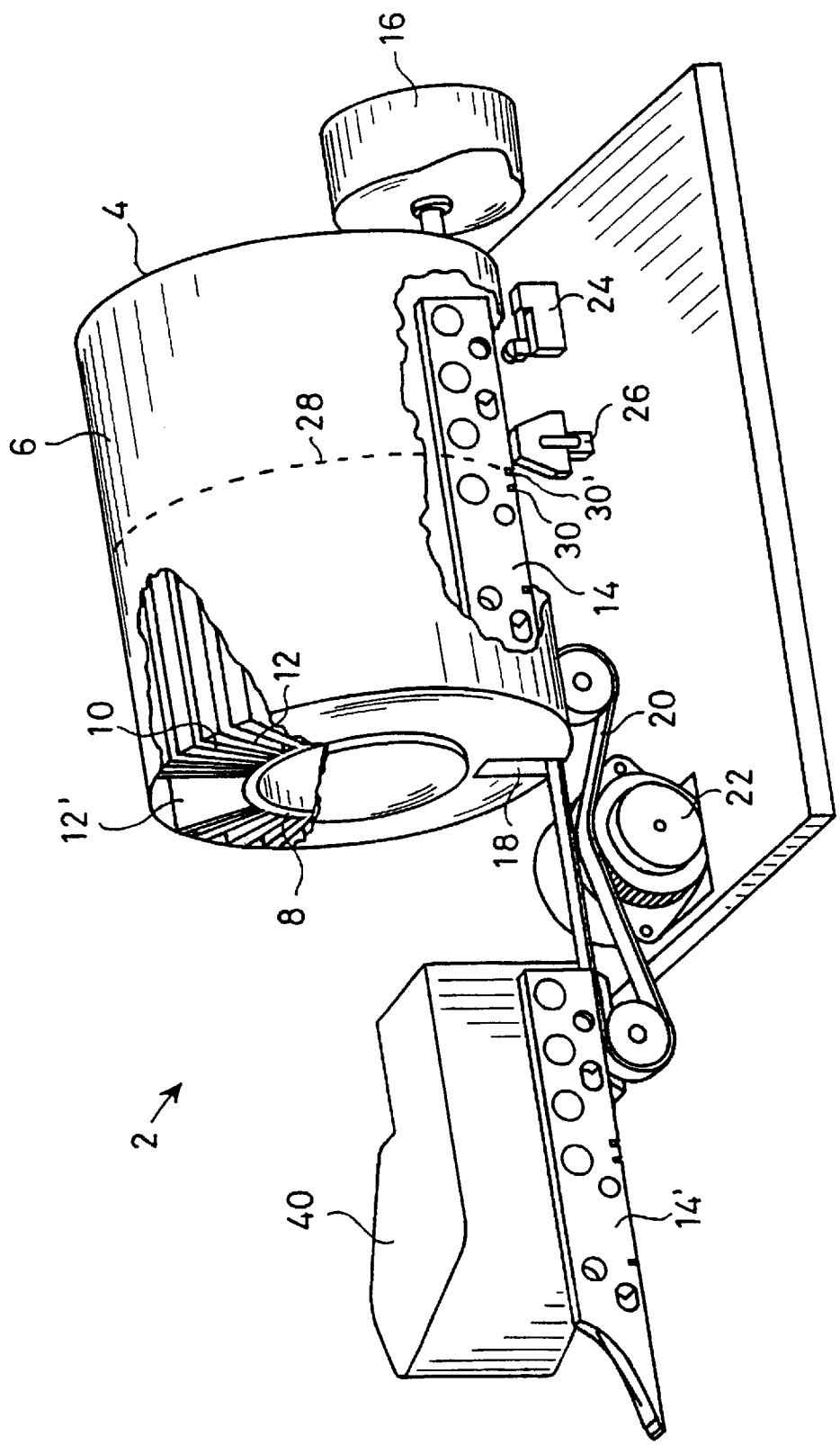

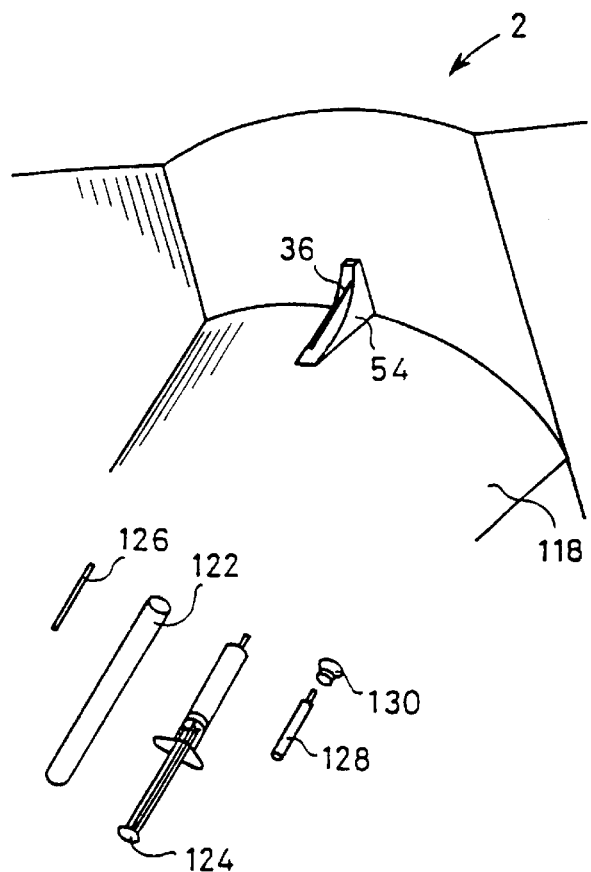
Fig. 6
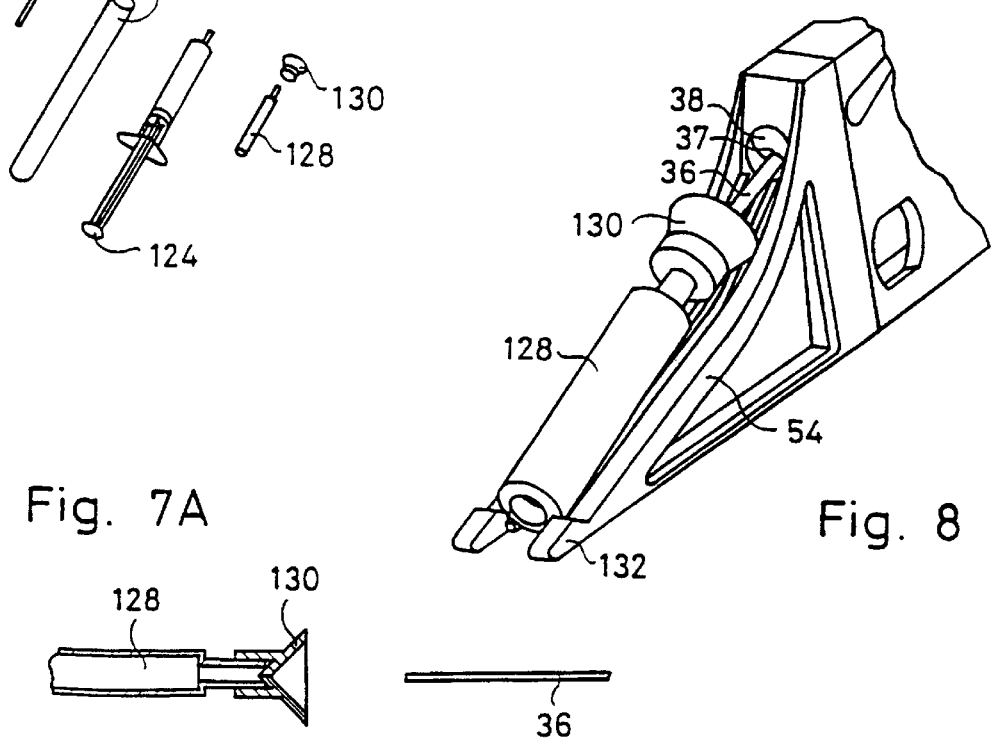
Fig. 8
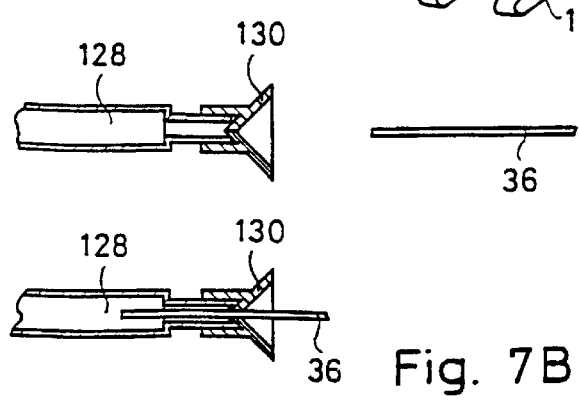
Fig. 7A
Fig. 7B

METHOD AND SYSTEM FOR DETERMINING AT LEAST ONE PARAMETER OF AT LEAST ONE SAMPLE OF A PHYSIOLOGICAL LIQUID, A HOLDER AND A TEST DEVICE

The present invention relates to a method for determining at least one parameter of samples of physiological liquids, to test devices which may be used in the method, to a holder comprising a plurality of such test devices, and to a measuring apparatus adapted to accommodate the holder and to be used in the method and to a system comprising the apparatus and the holder.

In particular, the present invention relates to methods and systems in which an operator, after sample taking, is protected from contact with physiological liquids, such as blood, plasma, urine, etc.

In human medicine, it has hitherto been customary practice to send samples of physiological liquids, e.g. blood, plasma or urine, for analysis to a specialized clinical laboratory possessing the necessary technical equipment and trained staff.

In the past, clinical chemical analysis systems have tended to be large in size, expensive and complex to operate, and in general only relatively large medical institutions have been able to afford the purchase, operation and maintenance of such systems. Smaller hospitals, clinics, general practitioners etc. usually have had to employ centralized commercial or hospital laboratories for clinical chemical analyses, leading to unavoidable delays in the procedure.

Since abnormal values of certain clinical chemical parameters are indicative of serious danger to health, the rapid and reliable determination of clinical chemical parameters in general is of crucial importance for proper and effective medical treatment. Furthermore, quite apart from the acute aspects of medical treatment, it is clearly an advantage, both for patients from a psychological viewpoint and for medical staff from an administrative viewpoint, that clinical analysis results are accessible as quickly as possible.

Thus, increasing demands for reduction in costs, more rapid turnover, greater decentralisation and increased staff flexibility in clinical chemical analysis have provided an incentive for the development of easy-to-use, easy-to-maintain, reliable, relatively cheap, compact and, if possible, portable equipment, based in part on discardable components, for the bedside measurement of those characteristics of chemical species which constitute fundamental clinical chemical parameters of physiological liquids.

In WO 89/04474, a portable apparatus for measuring the electrochemical characteristics of a sample is disclosed, which apparatus includes a shell which houses a cartridge bay adapted to receive, from a U-shaped clip, a plurality of disposable cartridges for receiving samples. A desired number of cartridges are manually loaded onto the clip and the clip is manually loaded into the cartridge bay whereby the cartridges are loaded into the apparatus. After loading, the clip is removed and discarded. A blood sample may now be dispensed into a specific cartridge in a measurement position in the apparatus from a sample containing syringe. After a measurement, the used cartridge is ejected from the apparatus.

It is a disadvantage of the above-mentioned apparatus that an operator and the environment of the apparatus is exposed to contact with the sample in a used cartridge after ejection of the cartridge from the apparatus.

The AVL Scientific Corporation has introduced the AVL OPTI 1 portable blood gas analyzer in which a disposable cassette adapted to receive a blood sample is inserted into the analyzer during a measurement. The blood sample may be supplied from a syringe or a capillary, which may be attached to the cassette and discarded with the cassette after a measurement. The disengagement and subsequent handling of this contaminated cassette is performed manually and, thus, subjects the operator to a risk of getting into contact with the sample.

It is an object of the present invention to provide a method and an apparatus for analysis of physiological liquids that provide maximum protection of laboratory staff from contact with a physiological liquid after sample taking.

It is another object of the present invention to provide a method and apparatus for analysis of physiological liquids in which a plurality of test devices can be inserted into the measuring apparatus in one operation and can be removed from the measuring apparatus in one operation whereby the number of manual operations needed to perform a determination of parameters of physiological liquids are minimized.

It is yet another object of the invention to provide a test device for use in a holder for holding the test device that both protect the environment from spills of samples and both provide maximum protection of laboratory staff from contact with physiological liquid after sample taking.

It is a further object of the invention to provide a test device adapted to receive and hold at least a part of a sampling device supplying the sample to the test device, so that the at least part of the sampling device can be discarded with the test device.

In a first aspect, the present invention relates to a method for determining at least one parameter of samples of physiological liquids, the method comprising arranging a plurality of test devices in a holder, loading, to at least one of the test devices, a sample of a physiological liquid, determining the at least one parameter of the sample loaded to the at least one test device, the at least one test device being retained in the holder after the determination, and discarding the holder with the at least one test device retained therein in such a manner that the at least one test device is substantially separated from the ambience, thus reducing the risk of contact between an operator and sample loaded to the at least one test device.

Parameters of physiological liquids of particular interest are, for example:

pH, concentrations of electrolytes, such as $Li^+$, $Na^+$, $K^+$, $Ca^{2+}$, $Mg^{2+}$, $Cl^-$, $HCO_3^-$ and $NH_3$ ($NH_4^+$), concentrations of dissolved gases, notably oxygen and carbon dioxide (conventionally reported in the form of partial pressures, e.g. $pO_2$, $pCO_2$), haemoglobin concentration, concentration of haemoglobin derivatives, concentrations of metabolic factors, such as glucose, creatinine, urea (BUN), uric acid, lactic acid, pyruvic acid, ascorbic acid, phosphate, protein, bilirubin, cholesterol, triglycerides, phenylalanine and tyrosine, concentrations of enzymes, such as lactic acid dehydrogenase (LDH), lipase, amylase, choline esterase, alkaline phosphatase, acid phosphatase, alanine amino transferase (ALAT), aspartate amino transferase (ASAT) and creatinine kinase (CK), and concentrations of ligands, such as antibodies and nucleotide fragments.

According to the present invention a parameter of a physiological liquid may be determined by any known suitable method, such as optical methods, such as measurement of absorption, scattering, diffraction, reflection, refraction, luminescence, fluorescence, phosphorescence, etc., in specific wavelength ranges of the electromagnetic spectrum, sensor response measurement methods, etc.

The term "sensor" as used here denotes any kind of organ of which some part, in the present context called the sensing part, is capable either of selective interaction with the chemical species of interest, thereby producing a well-defined and measurable response which is a function of the desired characteristic of that chemical species, the desired characteristic thus being derivable therefrom, or of response to a bulk property of a liquid, the response not being selective with respect to any specific chemical species, but being a function of the total concentration of one or more chemical species in the liquid, the desired characteristic thus being derivable therefrom.

Relevant types of sensors are those adapted to determine any of the previously mentioned clinical chemical parameters, for example:

potentiometric sensors for use in aqueous media, such as ion-selective electrodes for specific measurement of the concentration of selected ionic chemical species [a description of non-limiting examples of some ion-selective electrodes for the selective measurement of the concentrations of a number of cations and anions of frequent interest is provided by Simon (W. Simon, "Ion-Selective Electrodes Based on Neutral Carriers", in H. Freiser, Ed., "Ion-Selective Electrodes in Analytical Chemistry", Plenum, 1978, pp. 211–281)], the response being in the form of an electric potential, amperometric sensors, such as sensors for the determination of oxygen partial pressure, whose response is in the form of an electric current, optical sensors, such as sensors producing a colour response to a particular chemical species, the colour intensity being measured by, e.g., reflectometry, piezoelectric sensors, thermometric sensors, pressure-change sensors, acoustic sensors, enzyme-based sensors employing an enzymatic reaction and generating a response on the basis of any relevant physical principle, for example any of those principles employed in the sensor types listed above; examples are enzyme-based thermistors and enzyme-based amperometric sensors for use in the measurement of concentrations of metabolic products, e.g. glucose, urea, creatinine or lactate, and affinity sensors comprising one moiety of an affinity pair, e.g. an antigen/antibody pair or two complementary nucleotide fragments, the other moiety being the chemical species of interest.

Sensors generally perform a conversion function to convert the energy form associated with the change occurring at the sensing surface part to electrical energy or electromagnetic radiant energy, the sensor response thereby being registerable in the form of an electrical or optical signal. A more detailed description of non-limiting examples of conversion principles which are relevant in connection with sensors is given by Middelhoek & Noorlag (S. Middelhoek & D. J. W. Noorlag, "Three-Dimensional Representation of Input and Output Transducers", Sensors and Actuators 2, 1981/1982, pp. 29–41). The test device may have any appropriate configuration as described in the numerous patents, such as U.S. Pat. Nos. 4,053,381, 4,269,803, GB 2 090 659, WO 90/02938, U.S. Pat. No. 4,301,412, WO 89/04474, etc., and publications related to test devices or as commercially available. The sample may be loaded to a surface or a cavity of the test device.

It should be noted that the sample of the physiological liquid may be a pre-treated sample of the physiological sample. This pre-treatment may vary depending on the actual determination or determinations to be performed or the parameter or parameters to be determined. If a determination requires the addition of a reagent to the sample, this reagent may be added before the sample being loaded to the test device or it may be provided with the test device from the manufacturer.

In the event that the reagent will deteriorate other determinations, it may be preferred to add this reagent to e.g. a measuring chamber in the test device only used for the actual determination or only determinations not deteriorated by the agent.

Another factor to be taken into account is the timing of the addition of the reagent. It may be preferred to add the reagent as early as possible to either allow it to react with the sample in as large a period of time as possible or in order to e.g. prevent deterioration or alteration of the sample prior to determination.

An early addition of reagent may for example be obtained by having the reagent preloaded onto a sampling device used for the transfer of the sample from the patient to the test device. The reagent may be selected among compounds interacting with the chemical parameter or species under test and compounds needed for other purposes such as anticoagulants e.g. heparin, citrate or EDTA. Such anticoagulants are typically added to blood samples immediately after withdrawal of the blood from the patient.

According to this first aspect of the invention, the test device holding the sample is retained in a holder wherein the operator cannot gain access to the sample. When discarding the test device or test devices, the holder containing test devices is discarded. In this manner, the operator is not subjected to any hazards by these operations.

In the present context, the term that a test device is "substantially separated from the ambience" means that the test devices cannot accidentally leave the holder and that an operator cannot access the devices without using a tool.

It is an important advantage of the present invention that no parts of the test device can be accessed by an operator at the time where the operator has to remove or replace the device.

It is another advantage of the method according to the invention that the holder holds a plurality of test devices. Thereby, the operator need neither insert a new test device in the system nor remove a used test device from the system each time a determination of parameters has to be performed. Instead, a batch of test devices is inserted into the system in one operation and is removed from the system in one operation.

It is preferred that a plurality of samples of physiological liquids are introduced into respective test devices of the plurality of test devices, the at least one parameter of each sample is determined, the plurality of test devices loaded with samples the at least one parameter of which has been determined being retained in the holder, and that the holder is discarded with the test devices retained therein.

Thus, subsequent to determination of a parameter of a physiological liquid, the test devices are enclosed in the holder and inaccessible to the operator.

In order to further protect the operator from contact with physiological liquids, a sampling device for obtaining the sample from a patient or a part of the device may be received by the holder and discarded with the holder. For example, each test device may be adapted to receive and hold the sampling device or a part of thereof so that the (part of the) sampling device may be retained in the holder with the corresponding test device and may be discarded with the holder.

Even though access to any test devices in the holder which has not yet received a sample may not be hazardous to the operator (this depends on e.g. reagents present on or in the test devices for use in the determinations), it is preferred that a test device is transferred to an operational position prior to being loaded with a sample and that test devices not occupying an operational position are retained in the holder in such a manner that they are substantially separated from the ambience.

The test device may be adapted to receive and hold the sample in a liquid tight enclosure so that the sample is loaded to the device by introducing the sample into the device, e.g. by aspiration, and so that the environment and an operator is protected from contact with the sample.

A disinfectant may be provided in the test device. Most preferably the disinfectant is added to the test device during the manufacturing process. In the ready-to-use device the disinfectant may be present as a dry substance or in wet form and may be located in any suitable location in the test device. The presence of a disinfectant in the test device will prevent microbiological growth in the sample and among other things obviate or greatly reduce any smell inconveniences from spent test devices.

Further, a chemical substance detectable by the measuring apparatus per se or upon conversion may be provided to the test device as a label. When appropriately designed the measuring apparatus may be able to distinguish between labelled and unlabelled test devices.

This feature may be utilized to prevent use of non-authentic test devices.

In a second aspect, the invention relates to a system for determining at least one parameter of at least one sample of a physiological liquid, the system comprising a holder adapted to receive a plurality of test devices,
a measuring apparatus comprising
  means for receiving and operationally engaging with the holder,
  a measuring station comprising means for determining said at least one parameter of a sample loaded to a test device, and
  means for moving one or more test devices in the holder in relation to the measuring station so as to position individual devices held in the holder in operational communication with the measuring station,
the holder being adapted to substantially separate, from the ambience, any test device held therein loaded with a sample, thus allowing the holder with the sample-holding test device or devices to be discarded without any substantial risk of contact between an operator and the sample.

The term "operational communication" means that the measuring station and the one or more test devices is or are positioned in relation to each other in such a way that determinations of parameters of the sample(s) in the one or more test devices can be performed. The one or more test devices may be moved in relation to a fixed measurement station or the measurement station may be moved in relation to fixed test device(s).

Preferably, the present system comprises test device moving means for moving a test device which is to be moved into operational communication with the measuring station between a starting position in the holder, a sample loading position, and one or more measurement positions in which the test device is operationally positioned for measurement.

The holder may comprise a holder memory means for storage of data and the measuring apparatus may comprise means for reading the data contained in the holder memory means.

The data may comprise an expiry date of the test devices comprised by the holder, identification data, calibration data, etc.

Preferably, the means for reading data contained in the holder memory means comprise expiration date detection means for detection of the expiration date of the holder.

The system may prompt the operator, if a holder that is brought into engagement with the measuring apparatus of the system holds test devices which are no longer usable.

Further, the system may comprise first rejection means for preventing measurements with a holder containing test devices which have expired, to prevent that measurements using defective test devices are performed.

The means for reading data contained in the holder memory means may comprise detection means for detecting identification data of the holder.

The system may prompt the operator, if a holder with invalid identification data or no identification data is brought into engagement with the measuring apparatus.

The system may also comprise second rejection means for preventing measurements with a holder with invalid identification data or no identification data.

Different holders may hold test devices of different kinds, each kind of test device being adapted for determination of specific parameters. Each kind of test device may require the measuring system to execute specific operations during a determination. The holder memory means may contain data for specifying the specific operations to be executed by the measuring apparatus when in operational engagement with the corresponding holder.

In a third aspect, the present invention relates to a holder adapted to hold a plurality of test devices and having
  means for exposing at least one test device to measurement of at least one parameter of a sample loaded to the device, and means for substantially separating, from the ambience, any test device held therein loaded with a sample, thus allowing the holder with the sample-holding device or devices to be handled without any substantial risk of contact between an operator and the sample.

In the present context, "means for exposing at least one test device to measurement" may e.g. be one or more openings in the holder through which a measuring apparatus may gain access to the at least one test device, or it may be means for moving the at least one test device to a position in relation to a measuring apparatus or for moving a measuring apparatus to a position in relation to the at least one test device.

The holder preferably comprises a number of compartments each of which is adapted to hold one test device. Alternatively, the holder may comprise two compartments: for holding the unused and the used test devices, respectively.

Preferably, each compartment can change between a closed state, in which the test device(s) contained therein is/are substantially separated from the ambience, and an open state, in which the test device(s) contained therein is/are available to the ambience.

In order to reduce the risk of exposure of an operator to used test devices, preferably only one or a few of the compartments at a time can be in the open state.

The holder preferably holds a number of test devices being equal to or smaller than the number of compartments which are in a closed state, so that all contaminated test devices may be enclosed in the holder.

Preferably, the holder will comprise a holder housing and a holder member positioned in the holder housing.

A compartment in a closed state is preferably defined partly by structural elements of the member and partly by a wall part of the housing.

A compartment in an open state is preferably defined by structural elements of the member, the wall part of the housing co-operating with that compartment defining an opening therein allowing access of a test device contained therein to the ambience.

Even though virtually any shape and form of the holder may be contemplated, the presently preferred holder has a holder member being a substantially cylindrical drum positioned rotatably about a centre axis of the drum in the holder housing.

According to a preferred embodiment of the invention, the drum further comprises an inner cylindrical surface and a number of wall parts extending outwardly from the inner cylindrical surface, structural elements of the member partly defining the compartments comprising the outwardly extending wall parts.

The holder may comprise indicator means indicating the state of use of the test devices held in the holder. This is in particular advantageous when only a part of the test devices in the holder have been used when the holder is disengaged from the measuring apparatus. When the holder is re-engaged in the measuring apparatus, utilisation of the indicator means ensures that test devices containing samples are not brought into operational communication with the measuring apparatus.

The holder may comprise holder memory means for storage of data, such as an expiration date, calibration data of the test devices held in the holder, identification data, etc.

The holder memory means may comprise a bar code label or may comprise a more sophisticated electronic memory, such as a ROM, RAM, PROM, EPROM, $E^2$PROM, a magnetic strip, or an optically readable memory.

In order to further ensure that an operator cannot gain access to physiological liquid in the holder, such as sample spilled inside the holder, the holder preferably also comprises means for retaining sample wasted in the holder. These means may be positioned close to any openings of the holder, in order to prevent any spilled liquid sample to gain access to the outside of the holder.

A disinfectant may be provided in the holder. Most preferably the disinfectant is added to the holder during the manufacturing process. In the ready-to-use holder the disinfectant may be present as a dry substance or in wet form and may be located in any suitable location in the holder. The presence of a disinfectant in the holder will prevent microbiological growth in any sample waste and among other things obviate or greatly reduce any smell inconveniences from the holder.

In a fourth aspect, the present invention relates to a test device for receiving a sample of a physiological liquid and comprising a substantially sealed housing having a sample inlet port defined therein for entrance of the sample into the housing, the housing comprising at least one measuring chamber adapted for measurement of a parameter of a sample of a physiological liquid, and an extending member positioned at the sample inlet port, which member has a surface that is shaped to retain liquid, if wasted, on the member.

In the present context, "substantially sealed" means that access is, in fact, possible to the inner parts of the device in order to be able to introduce the sample therein, but that the device is able to, once the sample has been introduced therein, to hold substantially all sample therein, also during typical handing of the test device or a holder holding the test device.

When introducing liquid into standard test devices of the present type (holding the sample in a cavity), liquid may be spilled from the inlet port due to pressure or volume changes in the test devices or due to any movement thereof. This spilling of sample may be extremely hazardous to laboratory staff. Another problem may arise relating to sample spilled in the apparatus. This sample may constitute a hygiene hazard or problem and may furthermore cause problems if spilled on e.g. sensitive surfaces in the measuring instrumentation. These problems are reduced or avoided using test devices according to the invention.

Preferably, the surface of the extending member comprises one or more grooves so that liquid collected by the member is retained thereon by capillary forces. Naturally, also other types of surfaces, such as surfaces comprising a layer of cloth, felt or the like, may be used.

At present, it is preferred that the test device has an inlet probe positioned at the inlet port in fluid tight communication with the inlet port, the inlet probe having a first end proximate to the inlet port and an opposite second end, and that the extending member extends also to the second end of inlet probe and is adapted to retain liquid on the member if wasted from the second end. The inlet probe may facilitate easy aspiration of sample from a variety of widely used samplers or sample holders, such as syringes.

In order to also allow the use of e.g. capillary tubes, the inlet probe is preferably removably positioned at the inlet port in order to position the capillary directly at the inlet port when aspiring sample therefrom.

As described above, the parameter of the sample of a physiological liquid may be a blood gas parameter, such as $pO_2$, $pCO_2$, pH, haemoglobin, or derivatives of haemoglobin.

It is preferred that the extending member is positioned below the inlet port and/or inlet probe for optimal absorption and retainment of any sample spilled. However, a number of materials or surfaces will, if positioned sufficiently close to the position where the sample is wasted, be able to retain spilled sample, even if positioned at the side or above the inlet port.

A sampling device in which the liquid sample is transported from a patient to the test device or a part of the device may be received by the holder and discarded with the holder. For example, each test device may be adapted to receive and hold the sampling device or a part of thereof so that the (part of the) sampling device may be retained in the holder with the corresponding test device and may be discarded with the holder. The test device preferably comprises fastening means adapted to receive and hold at least a part of a liquid sampling device.

With the present method, system, holder and/or the test devices, spills of liquid sample during the relevant measuring steps is prevented or at least reduced and the number of elements contaminated with contents of the sample to be handled and/or disposed of is reduced and, thus, the risk of laboratory staff being exposed to the sample is greatly reduced.

Figure 2A:
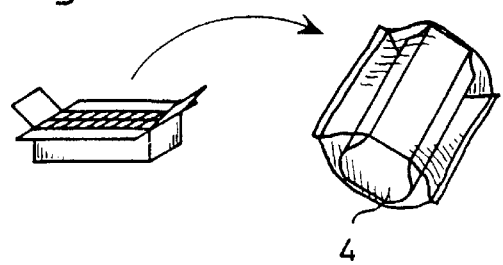
Figure 2B:
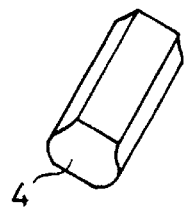
Figure 2C:
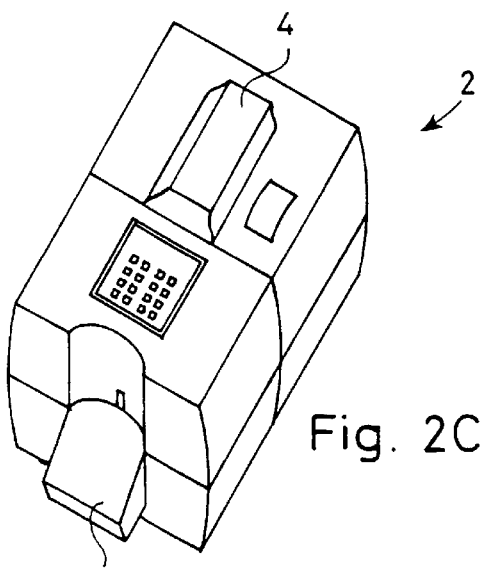
Figure 2D:
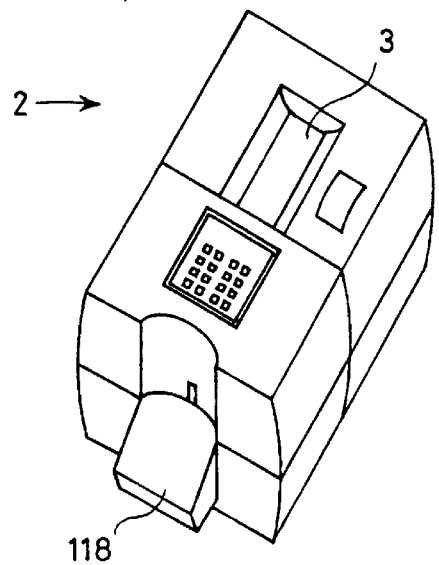
Figure 2D:
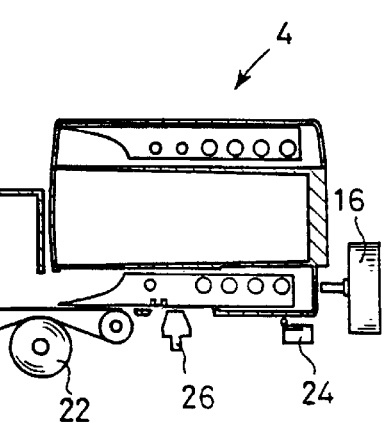
Figure 2E:
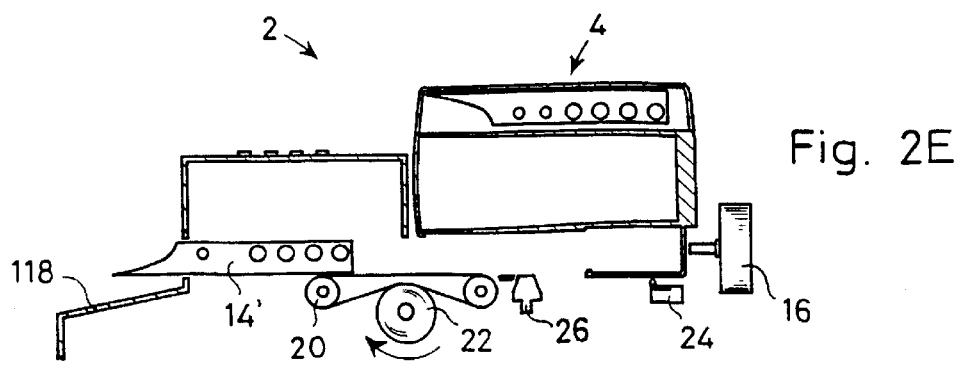
Figure 2F:
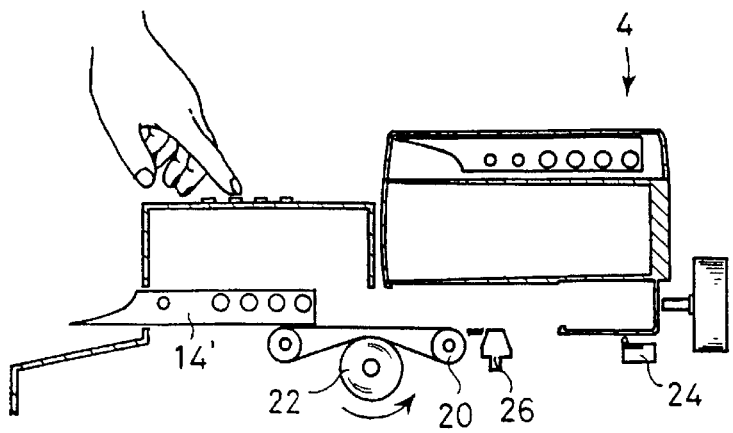
Figure 2G:
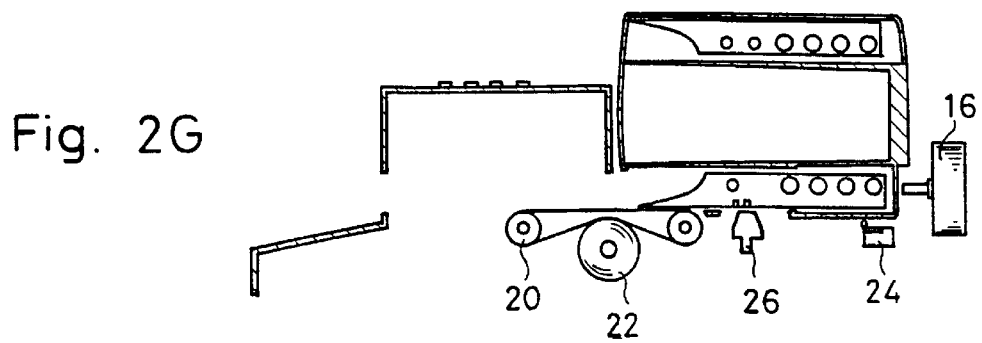
Figure 2H:
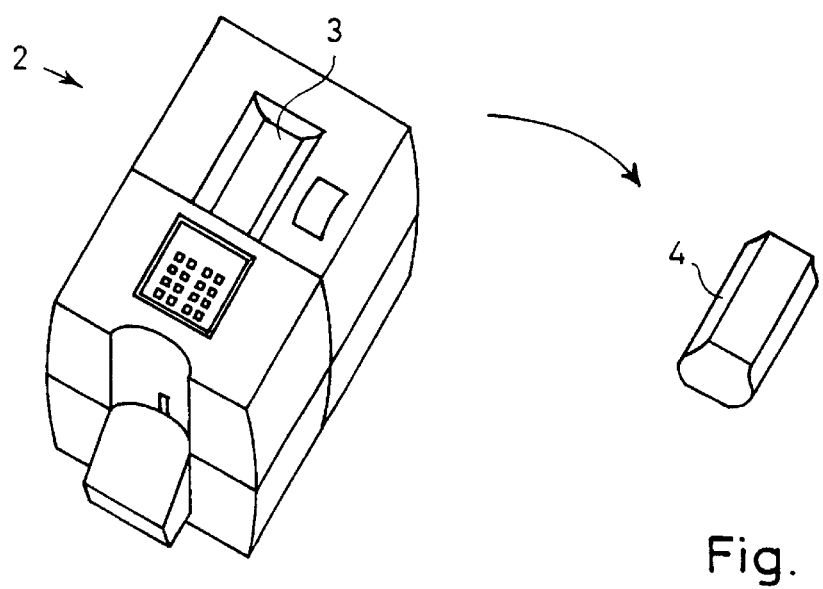
Figure 3:
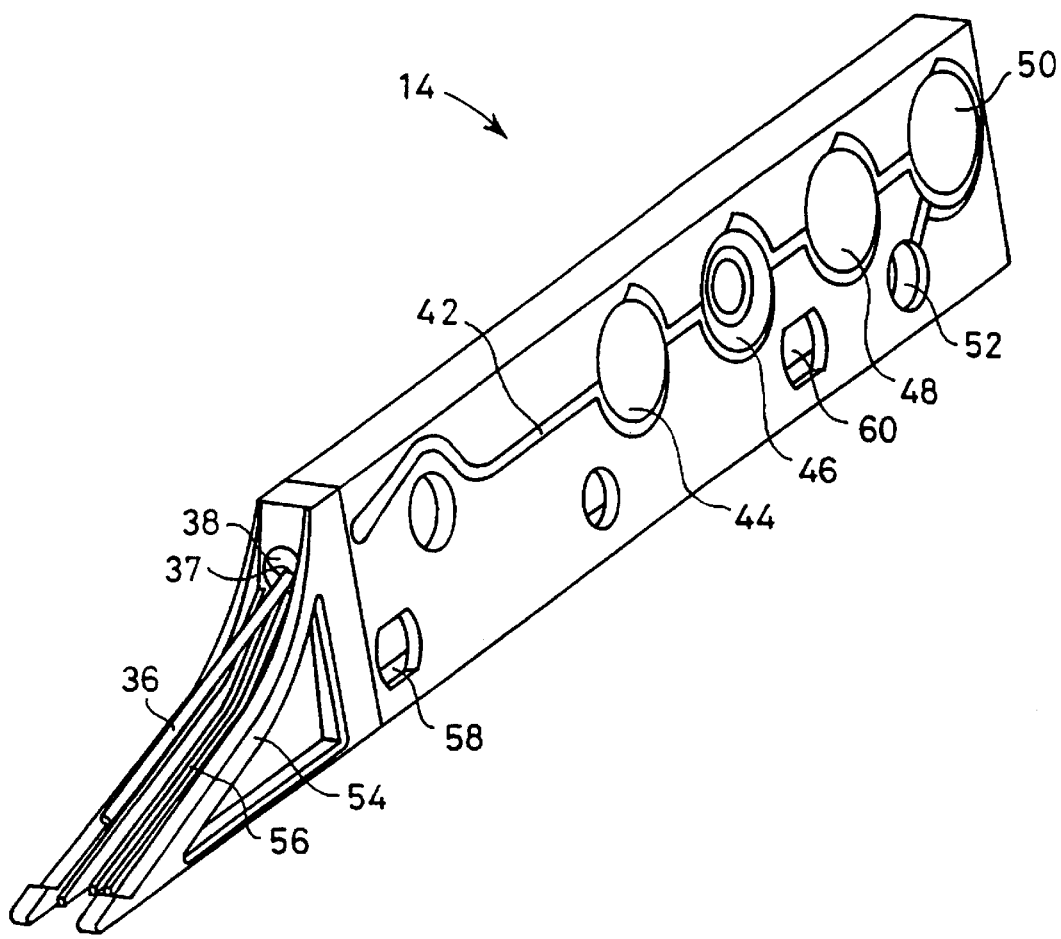
Figure 5:
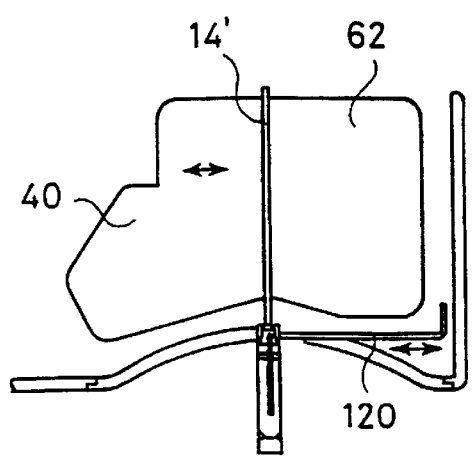
Figure 4:
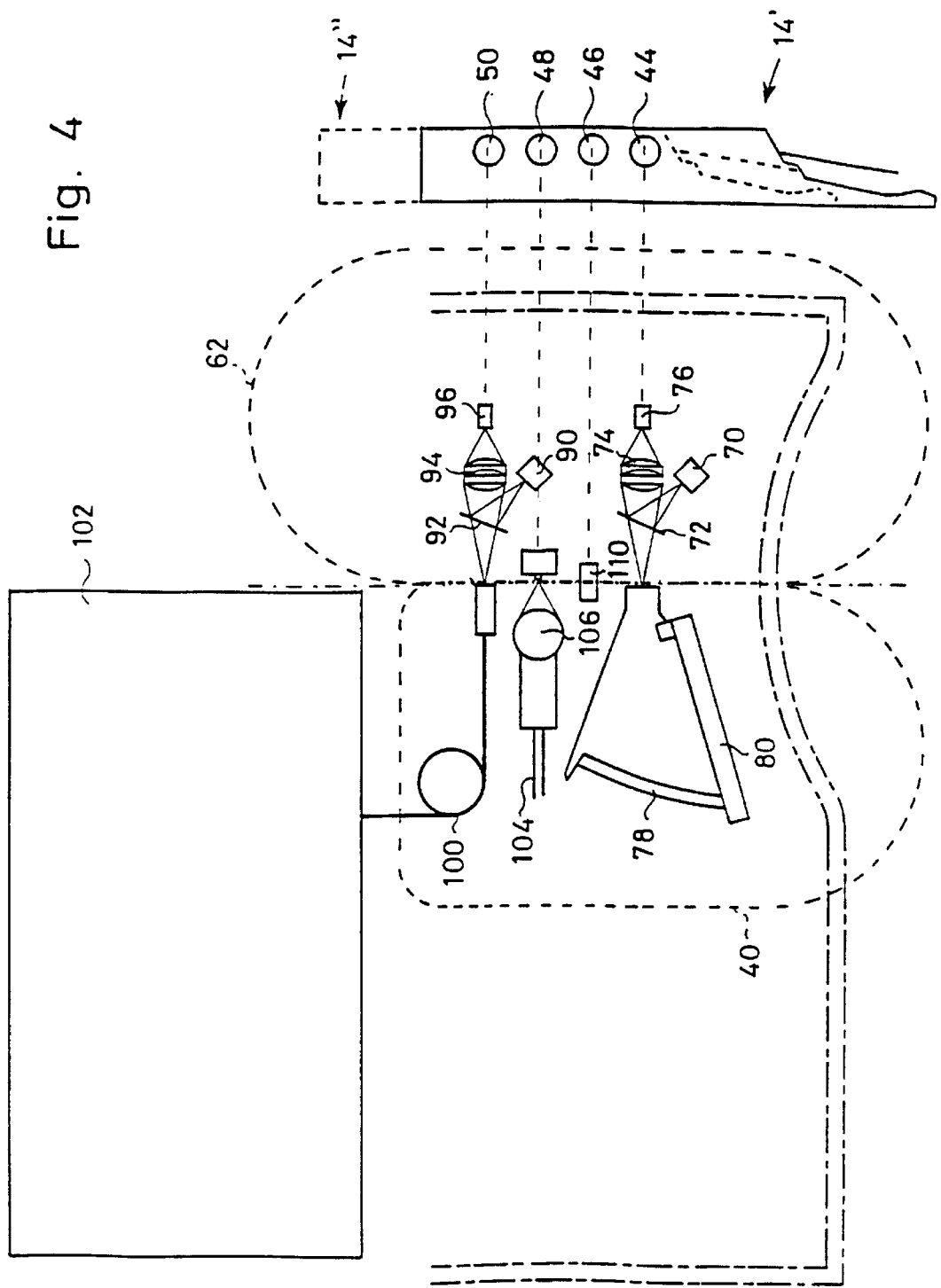

In the following, a preferred embodiment of the apparatus, a cassette (an embodiment of the holder), a cuvette (an embodiment of the test device) and the method according to the invention will be described for performing determination of parameters of physiological liquids and especially blood samples, with reference to the drawings, wherein:

FIG. 1 is a cut away view of a cassette and the cassette moving means of an apparatus according to the invention, FIGS. 2A–H, illustrate the overall use of the present apparatus and cassette from the point of view of the operator, FIG. 3 is an elevational side view of the presently preferred embodiment of the cuvette according to the invention, FIG. 4 illustrates the preferred embodiment of the optical elements used for performing the determinations of the parameters of the sample, FIG. 5 illustrates the overall operation of the detector unit and the power unit, FIG. 6, illustrates the front part of the apparatus where the sample collecting part of the cuvette extends out of the instrument and a number of sample collecting devices, FIGS. 7A and 7B illustrate a preferred sample collecting device with a cap and piercing of the cap so as to facilitate withdrawal of sample therefrom, and FIG. 8 illustrates the sample collecting device and the cap of FIGS. 7A and 7B in engagement with the cuvette of FIG. 3 in the position in which sample may be with-drawn from the container.

FIG. 1 is a cut away view of a cassette 4 and a cassette moving means 16 of an apparatus 2 according to the invention. From this figure, it may be seen that the cassette 4 comprises an outer casing 6 and an inner member consisting of an inner tubular member 8 and a number of radially extending fins 10. Between the members 8 and 10 and the inner surface of the casing 6, a number of compartments 12 are defined for holding a number of cuvettes 14.

The tubular member 8, the radially extending fins 10 and the cuvettes 14 are rotated with respect to the casing 6 by a motor 16 engaging the member 8 and the fins 10 in a known manner so as to provide rotation thereof.

In order to provide a cuvette 14 in the sample entry position 14' illustrated by a cuvette in that position, the motor 16 is activated in order to move an unused cuvette 14 into an operational position from which the cuvette 14 may be transported out of the casing 6 through an opening 18 therein. The transfer of the cuvette 14 from within the casing 6 to the sample entry position 14' is provided by a friction belt 20 engaging the lower side of the cuvette 14 and being driven by a motor 22. The sample entry position 14', introduction of a sample into the cuvette and measurement on that sample will be described further below.

The present apparatus 2 furthermore comprises a cassette detecting means 24 being a contact sensor upon which a force is exerted by the cassette 4 when positioned in the apparatus 2.

In addition, an optical censor 26 is provided for determining whether the cuvette 14 positioned in the operational position in the present figure has been previously used, i.e. contains a sample.

In the present embodiment, the cuvettes 14 in the cassette 4 are positioned in one of two possible longitudinal positions defined by a bead 28, the position of which is illustrated in the present figure as a broken line. The bead 28 preferably extends the full circumference of the casing 6 except for at a small distance at the position of the cuvette 14 in the operational position.

The bead 28 engages and extends into one of two notches 30 and 30' defined at the bottom of the cuvette 14 so as to ensure that a cuvette 14 positioned in a first position defined by the notch 30' and the bead 28 will not be able to be moved in any substantial degree in the direction of the longitudinal axis of the cassette 4 when being in any other angular position than the operational position in which the cuvette 14 may be moved out of the casing 6. The same applies for the second position defined by the bead 28 and the notch 30.

The detector 26 is preferably a reflection detector comprising a light emitter (not shown) emitting light onto the lower side of the cuvette and a light detector (not shown) which detects light reflected therefrom. Naturally, an opening or a transparent window should be provided in the casing 6 for the detector 26 to gain access to the lower side of the cuvette 14 in the operational position.

In the present embodiment, the detector 26 is positioned so that the reflection from the lower side of the cuvette 14 is different, when the cuvette 14 is in the first and second positions, due to the fact that, in the first position, the detector 26 will detect the reflection from a substantially plane part of the lower side of the cuvette 14, and, in the second position, the detector 26 will detect the reflection from the part of the lower side of the cuvette 14 comprising the notch 30'.

Thus, in the present embodiment, the first and second positions of the cuvette 14 define positions in which unused and used cuvettes, respectively, are positioned. Due to the engagement between the bead 28 and one of the notches 30 and 30', it is ensured that cuvettes positioned at other angular positions than the operational position may not shift between the used or unused positions.

The advantages of a set-up of the present type is that a cassette 4 in which not all of the cuvettes 14 have been used may be removed from the apparatus 2 and reinserted at a later date to use some of the unused cuvettes without using previously used cuvettes for new measurements.

When introducing a cassette 4 into the instrument 2, preferably an empty compartment 12 or a larger compartment 12' is positioned at the opening 18 in order to prevent access to the cuvettes or any blood spill in the cassette 4.

When instructing the instrument that the cassette 4 engaged therewith should be disengaged, the motor 16 is preferably operated to again position the empty compartment 12 or the compartment 12' at the opening 18 before disengaging the cassette 4 from the instrument.

When introducing a cassette 4 into engagement with the instrument 2, the instrument preferably operates the motor 16 to rotate the member 8, the fins 10 and the cuvettes 14 therein in order to determine (using the detector 26) how many unused and used cuvettes 14 are present therein.

In addition, this rotating movement may be used for reading e.g. a bar code provided to an outer surface of the rotating parts of the cassette 4, such as a substantially circular band (not shown) surrounding the outer circumference defined by the fins 10. This bar code may be read by a bar code reader (not shown) of the instrument 2 through an opening preferably positioned adjacent to the detectors 24 and 26.

Another embodiment of reading means for a bar code may be one in which the bar code is positioned on a substantially circular surface at the end of the cuvettes 14 and the compartments 12, such as a back end of the compartments 12 which is attached to the member 8 and/or the fins 10 so as to follow the rotating movement of the compartments 12. In this embodiment, the bar code reader may be positioned at the end of the cassette 4 closest to the motor 16 and again gain access to the bar code through an opening in the casing 6.

The bar code of the cassette may provide information relating to the production number, batch number, date a.s.o. which may be relevant in order to gain information relating to the durability, contents or use of e.g. the cuvettes 14. Different cuvettes 14 may be provided for different parameters to be determined or for different types of samples.

In addition, the bar code may comprise coded information ensuring that unauthorized cuvettes or cassettes are rejected by the instrument 2 so as to prevent malfunction thereof.

The cassette 4 may alternatively or additionally comprise a more versatile storage, such as a microprocessor based storage, a magnetic strip or another computer compatible storage, in which a larger amount of information may be stored and read and in which the instrument may write information for later use. This larger amount of information may, in addition to manufacturing and expiration dates etc. be information relating to calibration of the instrument etc.

In order to facilitate correct movement of the cuvette 14 from the unused, first operational position in the cassette 4 and to the sample entry position 14' and back to the used, second operational position, the motor 22 may be controlled in any known manner. This known manner may be a movement controlled by time, length of movement, angle of rotation of the motor shaft, or optical, electrical or mechanical means may be provided for determining when the cuvette 14 is in the position 14' and for terminating the movement.

In addition, the lower side of the cuvette 14 or a part thereof may comprise teeth and the belt 20 may be a toothed belt in order to further ensure that correct movement of the cuvette 14 to the position 14' is performed.

In the position 14', the cuvette 14 is engaged by a detector unit 40 and a power unit 62 (see FIG. 3) in order to introduce the liquid sample therein and to perform the measurement on the sample.

In FIGS. 2A–H, the operation of the present apparatus 2 is illustrated.

In order to provide a new cassette 4, one is provided from a storage, unwrapped (FIG. 2A) and introduced into a bay or recess 3 of the apparatus (FIG. 2B) in order to prepare an apparatus (FIG. 2C) for measurements. In FIG. 2D, a cross section is shown which illustrates the cassette 4 in engagement with the apparatus 2 and wherein a cuvette 14 has been moved, using the means 16, to the operational position so as to be ready for use. It is seen that the cuvette 14 is in the operational position in the first position populated only by unused cuvettes.

Subsequently (FIG. 2E), the cuvette 14 is transferred from the operational position in the cassette 4 to the sample entry position 14' by operating the motor 22. The cuvette in position 14' is now ready for introduction of a sample.

Introduction of a sample into the cuvette and measurement of the at least one parameter of the sample in the cuvette will be described further below.

After having performed the measurement, the cuvette in position 14' is returned to the cassette 4 by again operating the motor 22 (FIGS. 2F and 2G). In FIG. 2G it may be seen that the used cuvette in the operational 30 position is withdrawn to the second position populated only by used cuvettes.

In order to prepare the apparatus 2 for a new measurement, the motor 16 is again operated in order to rotate the used cuvette away from the operational position and to rotate a new, unused cuvette 14 into this position and operates the motor 22 in order to bring the cuvette to the sample entry position 14'. Thus, now the instrument is ready for performing the next measurement.

The instrument 2 may constantly calculate the number of used and unused cuvettes 14 in the cassette 4 and inform the operator thereof via e.g. a display (not shown).

In the situation where, subsequent to a measurement, all cuvettes 14 in the cassette 4 are used, the instrument 2 will rotate the member 8, the fins 10 and the cuvettes 14 so that an empty compartment 12 or the larger compartment 12' is positioned at the opening 18 and subsequently inform the operator that the present cassette 4 should be replaced (FIG. 2H). In the presently preferred embodiment, the operator is informed of the status of the instrument via a display (not shown) on the instrument. However, the operator might also or otherwise be informed by e.g. sound or via e.g. a computer connected to the instrument 2.

In FIG. 3, the presently preferred embodiment of the cuvette 14 according to the invention is illustrated in an elevational side view.

The cuvette 14 has a sample entry port 37 comprising a thin tube 36 engaging the body of the cuvette 14 through a resilient seal 38 for introducing liquid through the tube 36 and the seal 38 to a liquid path 42 providing liquid sample to four measuring chambers 44, 46, 48 and 50 and further to a filter 52. The filter 52 is adapted to engage a pump (not shown) for aspirating sample through the elements 36, 38, 42, 44, 46, 48 and 50 and to the filter 52.

Preferably, the filter 52 is a filter which in its dry state allows air or gas to pass and which becomes substantially impenetrable after having being in contact with a liquid. A presently preferred filter material (sold by Porex Technologies, Fairburn, USA) comprises a porous polyethylene plastic and sodium carboxymethyl cellulose which swells when brought in contact with water and subsequently becomes substantially impenetrable to gas and liquid. Optionally, a disinfectant is added to the filter 52.

Use of a filter of the present type has the advantage that substantially no part of the liquid sample can be transferred through the cuvette 14 to the pump, and that the pump may be operated and disengaged by simply monitoring the gas flow or the pressure at the pump entry and disengaging the pump when the gas flow or the pressure is reduced due to the filter 52 closing. In this manner, it is also ensured that the measuring chambers 44, 46, 48 and 50 are filled with the sample.

The individual measuring chambers 44, 46, 48 and 50 of the cuvette 14 are adapted to measurement of $pCO_2$, pH, $pO_2$ and $O_2Hb/tHb$ of blood, respectively. The preferred methods, the preferred cuvette materials and the preferred optical elements for use in these determinations are described in U.S. Pat. No. 5,371,020, European Patent specification No. 0 534 945, European Patent specification No. 0 449 899, and Danish patent No. 163 194, which are hereby incorporated by reference, and will therefore not be described in detail in the present specification.

At the sample entry port 37, the cuvette 14 furthermore has an extending portion or member 54 extending farther out and below the tube 36 in order to be able to collect any blood spilled from the tube 36 when introducing or subsequent to introduction of the liquid sample. In order to facilitate retainment of any blood spilled from the tube 36, the part 54 preferably comprises a number of grooves 56 which are adapted to hold any spilled sample by capillary forces.

Finally, the presently preferred cuvette 14 furthermore comprises indentations or holes 58 and 60 which are to be used for a first, coarse positioning of the cuvette 14 in the sample entry position 14' as illustrated in FIGS. 1 and 2E and as will be described below in connection with FIG. 5.

FIG. 4 illustrates the preferred embodiment of the combination of the optical elements described in the above patents issued to the applicant.

In the present figure, the cuvette 14 is shown on the right side of a power unit 62 for illustrating purposes. However, in operation of the instrument 2, the cuvette 14 is positioned at the dash-dotted line A between a detector unit 40 and the power unit 62 both illustrated by broken lines.

Thus, the optics provided for determining $pCO_2$ in the part of the sample present in measuring chamber 44 of the cuvette 14 is disclosed in U.S. Pat. No. 5,371,020 and comprise a custom-made filament 76, a chopper (not shown), a lens system 74, a partly reflecting mirror 72 and a reference detector 70. The light transmitted by the lens system 74 and not reflected by the partly reflecting mirror 72 is transmitted to the measuring chamber 44 and there through onto a curved mirror 78 and a grating 80 for finally being detected by a detector (not shown).

The optical elements required for performing a $O_2Hb$/tHb-measurement on the part of the sample present in measuring chamber 50 comprise a light emitter 96 (in the present embodiment a typical halogen lamp), a lens system 94, a partly reflecting mirror 92 and a reference detector 90. Light transmitted by the lens system 94, the partially reflecting mirror 92 and the measuring chamber 50 is collected and launched into an optical fibre 100 and transferred to an optical spectrometer 102 for analysis.

In FIG. 4, the optical elements provided for performing determination of $pO_2$ are illustrated by the box 104 and comprise typical elements for performing fluorescence measurements and may be seen from the applicants European patent No. 0 449 899. These optical elements are optically interconnected with measuring chamber 48 via a lens 106.

Due to the fact that the optical spectrometer 102 and the optical elements 90, 92, 94, 96 and 100 may be adapted for use for both the $O_2Hb$/tHb-measurement and the pH-measurement, it is presently preferred that these elements are used for both determinations. However, as the presently preferred pH-measurement requires the introduction of a pH-indicator in the sample, it is not preferred that these two measurements are performed on the same part of the sample. Therefore, in the present embodiment, $O_2Hb$/tHb-measurement is performed on the part of the sample present in the measuring chamber 50 of the cuvette 14 while in position 14' and the pH-measurement is performed on the part of the sample present in the measuring chamber 46.

Naturally, this requires a relative movement between the cuvette 14 and the optical elements 90, 92, 94, 96 and 100 in order to bring the measuring chamber 46 in operational engagement with these optical elements. Thus, it is preferred to transfer the cuvette 14 from the position 14' to a position 14" where this engagement is obtained. The position 14" is illustrated in broken lines in FIG. 4.

In addition, as it is desired that the part of the sample present in measuring chamber 46 is in chemical equilibrium with the indicator comprised therein before pH-determination is performed, it is presently preferred that this determination is made subsequent to the determinations of $O_2Hb$/tHb, $pO_2$ and $pCO_2$ and that, in the meantime, the measuring chamber 46 is contacted by thermostating means 110 in order to prepare the part of the liquid sample contained therein for the pH-determination.

Thus, subsequent to determination of $O_2Hb$/tHb, $pO_2$ and $pCO_2$, the cuvette is withdrawn to the position 14" so as to position the measuring chamber 46 at the position previously occupied by the measuring chamber 50 so as to bring the measuring chamber 46 into operational engagement with the optical elements previously used for the $O_2Hb$/tHb-determination. Subsequently, a pH-determination is made as described in the applicants European patent No. 0 534 945.

In FIG. 5, the overall operation of the detector unit 40 and the power unit 62, both indicated on FIG. 4 in broken lines, is illustrated.

In order to provide space for the cuvette 14 when transferred from the cassette 4 to the sample entry position 14', which is the position in which the $O_2Hb$/tHb-, $pO_2$- and $pCO_2$-determinations are made, therefrom to the position 14" in which the pH-determination is made, and therefrom back to the cassette 4, the detector unit 40 is displaceable in a direction transverse to the longitudinal direction of the cuvette 14.

When moving the detector unit 40 towards the cuvette 14, pins (not shown) are provided in the detector unit 40 for engaging the holes or indentations 58 and 60 of the cuvette 14 illustrated in FIG. 3, whereby a coarse positioning of the cuvette 14 takes place in the position 14' in relation to the power unit 62 and the detector unit 40 so as to position the measuring chambers 44, 46, 48 and 50 substantially correctly in relation to the optical elements' used for the measurements (see above).

Subsequent to moving the detector unit 40 into an operational position adjacent to the cuvette 14, the engaging and modulating elements described in the applicants above-mentioned patents are transferred from an inoperational position to an operational position in which they engage or at least approximate the optical windows of the measuring chambers 44, 46, 48 and 50. Due to the engagement of cones on part of these elements and cone-shaped surfaces of the measuring chambers 44, 46, 48 and 50, a fine adjustment of the position of the cuvette 14 is obtained.

In addition, when the optical elements of the detector unit 40 and the power unit 62 are in engagement with the cuvette in position 14', a pump (not shown) comprised in the power unit 62 operationally engaging the filter 52 via a seal (not shown) is operated in order to facilitate sample introduction.

A practical detail seen from FIG. 5 is that a moveable shield 120 is preferably provided in order to prevent access to the detector unit 40 and the power unit 62 through the opening provided for the cuvette 14 in the position 14' in the absence of a cuvette in that position.

The presently preferred cuvette 14 is manufactured so as to be able to withdraw samples (mostly blood) from a number of standard sampling or sample collecting means usually used in e.g. hospitals or laboratories.

In FIG. 6, part of the front of the apparatus 2 is illustrated where the sample inlet part of the cuvette 14 is in the sample entry position 14' and where the tube 36 and the front part 54 extend out of the instrument 2. In addition, a variety of sample collecting devices 122, 124, 126 and 128 are illustrated. These devices are used for transporting the blood sample from e.g. the patient to the instrument 2.

The tube 36 of the presently preferred cuvette 14 is adapted to be introduced into standard test tubes 122 or standard blood collecting syringes 124. In addition, as described above, as the tube 36 engages the body of the cuvette 14 through a resilient seal 38, the tube 36 is preferably removable in order for the cuvette 14 to be able to withdraw blood collected in a capillary tube 126 by removing the tube 36 and pressing the capillary tube 126 toward the resilient seal 38.

Preferably, the front part of the instrument 2 is designed so that an operator may be able to support a hand thereon (such as on the surface 118) while holding the test tube 122, the syringe 124 or the capillary tube 126 during introduction of the sample into the instrument 2. This will help preventing spills of the sample and will ensure optimal engagement between the cuvette 14 and the sample holding device (122, 124 or 126) during sample entry. This also helps to prevent air from being drawn into the cuvette and any malfunction of the instrument 2 caused thereby.

In addition, the front part of the cuvette 14 is preferably designed so that any test tube 122, syringe 124 or capillary tube 126, from which a sample is drawn, is not automatically able to engage the cuvette 14 and is therefore not prone to be withdrawn into the instrument 2 during withdrawal of the cuvette 14. Withdrawal of such elements into or partly into the instrument 2 may cause malfunction thereof. In fact, preferably the front part of the cuvette 14 is designed so that such elements will automatically fall from the instrument 2 if they are not removed by the operator.

However, in order to complete the task performed by the present instrument 2, cassette 4 and cuvettes 14 to enclose and contain the blood samples in a manner so that an operator cannot be exposed thereto, it may be desired that also the sample collecting device in which the sample is transported to the instrument 2 is also withdrawn into the cassette 4. This will further reduce the number of additional elements contaminated with the sample and which should be disposed of with the care required due to the samples probably being hazardous to the operator.

Therefore, a small custom-designed sample container 128 may be provided in which the blood sample may be transported from the patient to the instrument 2. After having introduced the blood sample into the container 128 (which may be pre-loaded with an anticoagulant or a reagent required for the subsequent test), a cap 130 may be applied in order to prevent spill of the sample during transportation thereof.

In FIG. 7A, the sample container 128 with a cap 130 is illustrated. The step of introducing the sample from the sample container 128 into the cuvette 14 preferable comprises piercing the cap 130 with the tube 36 as is illustrated in FIG. 7B.

The cap 130 may be any type of breakable or pierceable cap, such as a cap made of moulded rubber or simply a foil cap. Preferably, the cap 130 is of a type which, subsequently to piercing with the tube 36, provides sufficient friction between the cap 130 and the tube 36 so that the sample container 128 will not under normal circumstances by itself disengage and fall from the tube 36.

On the other hand, in order to facilitate withdrawal of the sample in the container 128 without generating an excess vacuum therein, it is preferred that the cap 130 allows air passage to the inner space of the container 128.

In FIG. 8, the sample container 128 and the cap 130 are illustrated in engagement with a cuvette 14 in a position in which sample may be withdrawn from the container 128. It is seen that the container 128 and the cap 130 are dimensioned so that they do not to any substantial degree extend beyond the dimensions of the cuvette 14, so that the instrument 2 and the cassette 4 will easily facilitate transportation and enclosure of the cuvette 14 when being in engagement with the container 128 and the cap 30. Naturally, the elements of the instrument 2 and the cassette 4 may be adapted to any desired shape and any desired dimensions of a container 128.

In order to further ensure that the container 128 is not accidentally released from the cuvette 14, the front part 54 of the cuvette 14 may comprise projections 132, which support the container 128 at a lower end thereof.

In the present embodiment of the instrument and the cuvette according to the invention, a total sample volume of 100 µl is required in order to fill the liquid path 42 and the measuring chambers 44, 46, 48 and 50 of the cuvette 14. Thus, the custom-designed sampler 128 is preferably designed to contain 100–300 µl, such as 250 µl.

Thus, by providing a sample container 128 and a suitable cap 130 therefore, the amount of blood contaminated waste generated by the obtaining of, transport of and the determination of parameters in a blood sample may be reduced to, in fact, only a blood collecting needle, if a such has been used, due to the fact that all other blood contaminated elements may be fastened to the cuvette 14 and withdrawn into the cassette 4, where the operator cannot accidentally gain access to the contaminated blood.

An additional advantage of the container 128 is that any quality control liquid desired or required by the instrument 2 may be provided in similarly shaped containers and may therefore be introduced into the cassette 4 after use, without any additional waste being generated during quality control of the instrument 2.

In order to ensure that any blood spilled from the cuvettes 14 present in the cassette 4, such as during handling thereof or rotation of the cuvettes 14 therein, all areas 23 of the casing 6 thereof close to openings therein (such as the opening 18) may be provided with inwardly directed edges and/or with absorbing faces such as surfaces covered with e.g. felt or cloth or surfaces covered with e.g. grooves for absorbing blood by capillary forces, in order to ensure that any blood spilled within the casing 6 is not able to flow to the outside of the cassette 4, where an operator may gain access thereto.

What is claimed is:

1. A method for determining at least one parameter of at least one sample of a physiological liquid, the method comprising the steps of:

arranging a plurality of test devices in a holder, wherein each test device comprises a substantially sealed housing having a sample inlet port for entrance of the sample into the housing of the test device, and the housing comprising at least one measuring chamber adapted for measurement of the at least one parameter of the sample and an extending member positioned at the sample inlet port, the extending member having a surface that retains the physiological liquid, if spilled, on the extending member;

loading, to the at least one test device, the sample of the physiological liquid;

determining the at least one parameter of the sample loaded; and discarding the holder with the at least one test device, retained in the holder wherein the at least one test device is substantially separated from the ambience.

2. The method according to claim 1, wherein a plurality of samples of physiological liquids are loaded into respective test devices of the plurality of test devices in the holder, and the holder is discarded with the plurality of test devices retained in the holder.

3. The method according to claim 1, wherein the at least one sample is loaded to the at least one test device from a sampling device or part thereof that conveys the at least one sample, and the sampling device or part thereof that conveys the at least one sample is received by the holder and discarded with the holder.

4. The method according to claim 1, wherein the at least one test device is transferred to an operational position prior to being loaded with the sample and further wherein test devices not occupying an operational position are retained in the holder and arc substantially separated from the ambience.

5. The method according to claim 1, wherein the at least one parameter of the sample is a blood gas parameter.

6. The method according to claim 5, wherein the blood gas parameter is $pO_2$, $pCO_2$, pH, hemoglobin, or derivatives of hemoglobin.

* * * * *

UNITED STATES PATENT AND TRADEMARK OFFICE
CERTIFICATE OF CORRECTION

PATENT NO.    : 6,605,471 B1
DATED         : August 12, 2003
INVENTOR(S)   : Lundsgaard et al.

It is certified that error appears in the above-identified patent and that said Letters Patent is hereby corrected as shown below:

Column 16,
Line 59, please change "arc" to -- are --.

Signed and Sealed this

Twenty-eighth Day of October, 2003

JAMES E. ROGAN
*Director of the United States Patent and Trademark Office*